(12) United States Patent
Lortal et al.

(10) Patent No.: US 6,902,749 B1
(45) Date of Patent: Jun. 7, 2005

(54) KLUYVEROMYCES LACTIS AS ATTENUATED STARTER

(75) Inventors: Sylvie Lortal, Rennes (FR); Nathalie Klein, Sarreguemines (FR)

(73) Assignee: DSM IP Assets B.V., Heerlen (NL)

( * ) Notice: Subject to any disclaimer, the term of this patent is extended or adjusted under 35 U.S.C. 154(b) by 306 days.

(21) Appl. No.: 10/111,363

(22) PCT Filed: Oct. 26, 2000

(86) PCT No.: PCT/EP00/10627

§ 371 (c)(1),
(2), (4) Date: Apr. 5, 2002

(87) PCT Pub. No.: WO01/30172

PCT Pub. Date: May 3, 2001

(30) Foreign Application Priority Data

Oct. 28, 1999 (EP) ............................................. 99203555

(51) Int. Cl.[7] .......................... A23C 19/032; C12N 1/16
(52) U.S. Cl. ....................................... 426/37; 435/255.1
(58) Field of Search ........................ 435/254.11, 255.1; 426/37, 42, 582

(56) References Cited

U.S. PATENT DOCUMENTS

| | | | | |
|---|---|---|---|---|
| 3,981,773 A | * | 9/1976 | Galzy et al. ................... | 426/39 |
| 4,165,389 A | * | 8/1979 | du Chaffaut et al. .......... | 426/42 |
| 4,211,798 A | * | 7/1980 | Cater ........................... | 426/41 |
| 5,071,762 A | * | 12/1991 | Shay et al. ................... | 435/247 |
| 6,190,879 B1 | * | 2/2001 | Bech et al. .................. | 435/68.1 |
| 6,413,559 B1 | * | 7/2002 | Kauppinen et al. ............ | 426/20 |
| 6,649,199 B2 | * | 11/2003 | Bigret .......................... | 426/34 |

FOREIGN PATENT DOCUMENTS

| | | |
|---|---|---|
| EP | 0 167 309 | 1/1986 |
| EP | 0 415 470 | 3/1991 |
| FR | 2 694 766 | 2/1994 |
| WO | WO 92/00017 | 1/1992 |
| WO | WO 96/38549 | 12/1996 |
| WO | WO 98/48645 | 11/1998 |

OTHER PUBLICATIONS

Schmidt et al. "The yeasts of Camembert cheese . . . ". Abstract XP002133501. From Advances in Biotechnology, vol. II. International Fermentation Symposium (6th), 1981.*
Conner, "Advances in Accelerated Ripening of Cheese," *Cult Dairy Prod J* 23:21–25 (1988).
Doi et al., "Modified Colorimetric Ninhydrin Methods for Peptidase Assay," *Anal Biochem* 118:173–184 (1981).
El Soda et al., "Acceleration of Low–Fat Cheese Ripening Using Lyophilised Extracts or Freeze Shocked Cells of some Cheese Related Micro–Organisms," *Milchwissenschaft* 46:358–360 (1991).
El Soda et al., "Recent Developments in Accelerated Cheese Ripening" *J Dairy Sci* 74:2317–2335 (1991).
Ferranti et al., *Lait* 77:683–697 (1997).
Fox, "Proteolysis During Cheese Manufacture and Ripening," *J Dairy Res* 72:1379–1400 (1989).
Gao et al., "Aromatic Amino Acid Catabolism by Lactococci," *Lait* 77:371–381 (1997).
Gobbetti et al., "Esterolytic and Lipolytic Activities of Mesophilic and Thermophilic lactobacilli," *It J Food Sci* 2:127–137 (1996).
Gouldsworthy et al., *Int Dairy J* 6:781–790 (1996).
Grieve et al., "Partial Characterization of Cheese–ripening Proteinases Producted by the Yeast *Kluyveromyces lactis*," *J Dairy Res* 50(4):469–480 (1983).
Law and Haandrikman, "Proteolytic Enzymes of Lactic Acid Bacteria," *Internat Dairy J* 7:1–11 (1997).
Lemée and Maubois, "Strain Variability of the Cell–free Proteolytic Activity of Dairy Propionibacteria towards β–Casein Peptides," *Lait* 78227–240 (1998).
Lowry et al., "Protein Measurement with the Folin Phenol Reagent," *J. Biol Chem* 193:265–275 (1951).
Martin et al., "Flavor Generation in Cheese Curd by Coculturing with Selected Yeast, Mold, and Bacteria," *J Dairy Sci US* 82(6):1072–1080 (1999).
Mondino et al., "An Improved Method of Plasma Deproteinisation with Sulphosalicyclic Acid for Determining Amino Acids and Related Compounds," *J Chromoto* 74 : 225–263 (1972).
O'Sullivan et al., Evaluation of Microbial Chymosin from Genetically Engineered *Kluyveromyces lactis, Food Biotech* 5(1):19–32 (1991).
Petterson and Sjöström, "Accelerated Cheese Ripening. A Method of Increasing the Number of Lactic Starter without Detrimental Effect of the Cheese–Making Process and its Effect on Cheese Ripening," *J Dairy Res* 42:313–326 (1975).
Shakeel–Ur–Rehman et al., "Protocol for the Manufacture of Miniature Cheeses," *Lait* 78:607–620 (1998).
Transfiguracion et al., "Purification and Characterization of Carboxypeptidase Y from *Kluyveromyces fragilis* JSB95," *J Dairy Sci* 81(3):647–654 (1998).
Tye et al., "Effects of Bacterial Protese on the Qualify of Cheddar Cheese," *Can Inst Food Sci Technol J* 21:373–377 (1988).
Urbach, "Contribution of Lactic Acid Bacteria to Flavour compound Formation in Dairy Products," *Int Dairy J* 5:877–903 (1995).
Yvon and Gripon, "Adding α–keto–glutarate to Semi–hard Cheese Curd Highly Enhances the Conversion of Amino Acids to Aroma Compounds," *Int Dairy J* 8:889–898 (1998).

* cited by examiner

*Primary Examiner*—Keith Hendricks
(74) *Attorney, Agent, or Firm*—Morrison & Foerster LLP

(57) ABSTRACT

A process for producing cheese, cheese analogues and cheese-derived products comprises contacting said cheese, analogues or products with a *Kluyveromyces lactis* cell or an enzyme derived therefrom.

7 Claims, 2 Drawing Sheets

KLUYVEROMYCES LACTIS AS ATTENUATED STARTER

FIELD OF THE INVENTION

This invention relates to a process for producing cheese, cheese analogues and cheese-derived products, and more particularly to a method to enhance the rate of taste, flavour and texture formation and/or to extend the range of tastes, flavours and textures.

DESCRIPTION OF THE PRIOR ART

Eating habits in the World show an increased use of cheese and other fermented milk products. There exists an enormous variety in types of cheese, cheese analogues and cheese-derived products and, consequently, in production methods to obtain those products.

The production of cheese starts with the clotting of milk, which is provoked by the specific proteolytic action of chymosin or similar enzymes, such as those found in rennets of animal or microbial origin. Lactic acid bacteria (i.e. starters such as Lactococci) are added in order to get the required acidification of the milk depending on the cheese technology involved. The resulting curd is composed mainly of the casein together with milk fat droplets that are entrapped by inclusion. A substantial fraction of the rennet and the lactic acid bacteria also ends up in the curd. After pressing the whey to reduce the water content, the young cheese is subjected to a process of ripening in order to give the final cheese its desired taste, flavour and texture.

The formation of taste, flavour and texture of cheese, cheese analogues and cheese-derived products is a process that involves complex and well-balanced reactions between glycolysis, proteolysis and lipolysis of the milk components and further degradation of amino acids. The degradation products of the milk fat and protein (peptides, free amino acids, di- and mono-glycerides, free fatty acids and amino acid derived compounds such as amines, ketoacids, aldehydes, ketones, alcohols, esters, acids and sulphur compounds) all contribute to the specific taste-, flavour- and texture properties of the cheese in question.

Proteolysis during ripening of cheese can be extensive (Fox, 1989). In hard cheese, 25–35% of the insoluble protein of the curd may be converted into soluble protein. In soft varieties such as Brie, Camembert or Limburger, over 80% of the insoluble protein can be converted to water-soluble compounds such as peptides, amino acids and ammonia (Foster et at. 1983).

Flavour formation in cheese, cheese analogues and cheese-derived products is a process involving a cascade of enzymatic reactions. Starting from amino acids, compounds including amines, ketoacids, aldehydes, ketones, alcohols, esters, acids and sulphur compounds can be formed as intermediate products and/or final flavours. Decarboxylation of amino acids results in the formation of the corresponding amines and is catalysed by various decarboxylases from the enzyme class EC.4.1.1. Specific examples are lysine decarboxylase $(EC.4.1.1.18)_1$ arginine decarboxylase (EC.4.1.1.19), histidine decarboxylase (EC.4.1.1.22) and various others. Subsequently, the amines can be converted to the corresponding aldehydes and ammonia by oxidative deamination involving enzymes such as amine oxidases (EC.1.4.3.6). Aldehydes can be further oxidised to the corresponding acids by aldehyde dehydrogenases of class EC. 1.2 (subclasses are formed according to the electron- and/or hydrogen acceptor) or reduced to the corresponding alcohols by alcohol dehydrogenases (EC.1.1—subclasses are formed according to the electron- and/or hydrogen donor). Alternatively, amino acids can be converted via deamination and transamination reactions. Deamination results in the corresponding alpha-ketoacids and ammonia and requires the action of amino acid oxidases or dehydrogenases such as EC.1.4.1.5 and EC.1.4.3.2. Transamination also results in the corresponding alpha-ketoacids but the amino-group is transferred to another accepting ketoacid (e.g. alpha-ketoglutarate or oxaloacetate) with a concomitant transfer of the oxygen group from the accepting ketoacid to the amino acid. In this case no ammonia is liberated. This reaction requires the action of various aminotransferases also named transaminases, from the enzyme class EC.2.6.1. The ketoacids formed by deamination and transamination of amino acids can be further converted to aldehydes by decarboxylation involving various decarboxylases from the enzyme class EC.4.1.1

In normal (i.e. not accelerated) processes, the formation of taste, flavour and texture is effectuated by endogenous milk enzymes such as plasmin and by exogenous enzymes such as the rennet used for clotting. Furthermore, starter cultures such as lactic acid bacteria used for the initial acidification of the milk, also contribute to cheese ripening because a substantial fraction of the bacteria usually ends up in the curd. Their combined extracellular proteolytic- and intracellular peptidolytic activities and enzymes that further degrade amino acids into the compounds listed above, are capable of breaking down the casein fraction. The proteases, peptidases, esterases, lipases and the enzymes of amino acid catabolism in the lactic acid bacteria have been extensively studied (Urbach, 1995: Gobbetti et al., 1996; Gao et al., 1997; Law and Haandrikman, 1997). However, those of other starters, such as propionibacteria and surface flora, have been studied much less extensively.

A common disadvantage in most of the production methods is that the ripening process, i.e. the process of taste, flavour and texture formation, very long, extending from days up to several months and in some instances years. For economic reasons, a shorter ripening time is highly desirable. Acceleration of ripening is most pertinent for low-moisture, slow ripening varieties and most published work has been done on cheddar (Fox et al., 1996). In addition, there is an industrial need for increasing the range of types of taste, flavour and texture of cheeses, cheese analogues and cheese-derived products.

Enhancement of the rate and extent of taste, flavour and texture formation and increasing the range of tastes, flavours and textures can be achieved by either adding additional bacteria or by adding additional enzymes.

Changing the lactic acid bacterial enzyme content in cheese directly affects the rate said ripening and the final flavour. One of the most efficient ways to increase the bacterial enzyme pool in cheese curd, without altering the primary starter and the cheese make, is to add whole lactic acid bacteria which are unable to grow and to produce significant quantities of lactic acid, but which can still deliver active ripening enzymes during the ripening stage. These starters are called "attenuated".

Attenuated starters can be prepared by various treatments like heating, freezing, spray drying, freeze-drying, fragilization using lysozyme or solvents, or by the selection of lactose negative mutants treatment (see Klein and Lortal for a recent review). Pettersson and Sjöström reported the first preparation and use of attenuated starters as a cheese additive, in 1975. At that time, their main purpose was to accelerate proteolysis and shorten ripening time, which was of great economic interest. Today, in most developed countries the hygienic quality of milk is so high that the problem is not only to shorten the ripening time but also to improve the flavour. This is particularly true for new kinds of cheeses such as those made from UF- or low-fat milk, which usually exhibit poor flavour development and a rubbery texture (El Soda et al., 1991). Attenuated starters if they are well known and reproducibly made, can improve both the rate and the quality of cheese ripening (Fox, 1988; El Soda and Pandian, 1991).

Enzymes such as proteases and lipases are used for manufacturing cheese, cheese analogues and cheese-derived products in which the rate of formation of taste, flavour and texture is enhanced and the range of tastes, flavours and textures extended significantly (Conner, 1988; Tye et al. 1988). International Patent Application WO 96/38549 discloses the use of an *Aspergillus* aminopeptidase and European Patent Specification EP 0167309 discloses the use of a fungal lipase. In general, these flavour enhancing enzymes can be added in the form of attenuated bacteria (vide supra), as a paste (Kosikowski, 1988), as solutions (Law, 1980), through encapsulation techniques (Braun and Olson, 1986; Alkhalaf et al., 1988; El Soda et al, 1989), as soluble enzymes with salt (Green, 1985) or as enzymes themselves.

SUMMARY OF THE INVENTION

The present invention provides a process for producing a cheese, a cheese analogue or a cheese-derived product which process comprises contacting a cheese, a cheese analogue or a cheese-derived product or a precursor of any thereof with a *Kluyveromyces lactis* cell or an enzyme derived therefrom.

The invention also provides:
- a cheese, a cheese analogue or a processed cheese obtainable by a method of the invention;
- use of a *K. lactis* cell or enzyme derived therefrom in a process for producing a cheese, a cheese analogue or a cheese-derived product, and
- an attenuated *K. lactis* cell; and Typically, an attenuated yeast cell of the invention is characterised in that it may enhance the rate of taste-, flavour- or texture formation in a cheese, a cheese analogues, or a cheese-derived product and/or may extend the range of tastes, flavours or textures of those products.

The process of the invention producing a cheese, a cheese analogue or a cheese-derived product may result in an enhanced rate of taste-, flavour- or texture formation and/or an extension of the range of tastes, flavours or textures of the products produced.

DESCRIPTION OF THE INVENTION

By the term cheese we mean a dairy product belonging to: a soft cheese variety, for example, Camembert, Münster or Livanot; a semi-hard variety such as Torre de Savoie, Gouda, Edam or Mimolette; or a hard cheese variety such as Cheddar, Gruyere or the Swiss cheeses or Parmesan.

By the term cheese analogue we mean a product composed of: (i) dairy protein, for example casein or caseinate, and/or whey protein concentrate coagulated by acidification or by heat treatment and (ii) cheese flavouring agent.

By the term cheese-derived product we mean either a processed cheese, for example, a preheated mixture of cheeses, butter or other fatty materials, melting salts or any type of cheese curds to which enzymes are added in order to give desired texture- and flavouring properties.

By the term precursor we mean any substance that is present in the process of the invention which will ultimately become a cheese, a cheese analogue or a cheese-derived product. Thus a precursor could be milk, butter or cheese curds for example. A yeast cell or an enzyme derived therefrom may be contacted with a cheese, a cheese analogue or a cheese derived product or a precursor of any thereof at any point during the manufacture of one of those products. Thus, the yeast cell or an enzyme derived therefrom can be added to milk or alternatively could be added to a young cheese during ripening.

By the term ripening we mean the formation of taste, flavour and texture of a cheese, a cheese analogue, or a cheese-derived product. Ripening involves complex and well-balanced reactions including glycolysis, proteolysis and lipolysis of milk components and further degradation of amino acids in amines, ketoacids, aldehydes, ketones, alcohols, esters, acid and sulphur compounds by a cascade of enzymatic reactions, for example, decarboxylation, transamination, deamination, oxidation or reduction.

By the term yeast we mean a non-taxonomic category of fungi that is defined in terms of morphological and physiological criteria (P. Singleton, 1994). *Kluyveromyces lactis* is a unicellular saprotroph which can metabolise carbohydrates by fermentation and in which asexual reproduction occurs by budding.

By the term attenuated cell, we mean a cell, for example a bacterial, a fungal or a yeast cell, that has been treated in such a way that at least 80%, preferably more than 90% and more preferably 99% of the cells are killed but not lysed while more than 50%, more preferably more than 90% of the cell's intracellular enzyme activity, comprising the ripening enzymes proteases, peptidases, lipases, esterases, decarboxylases, aldehyde dehydrogenases, amino oxidases, alcohol dehydrogenases, amino acid dehydrogenases, amino acid oxidases, amino transferase and/or transaminases, is retained. Aminopeptidase activity can be used to determine how much enzyme activity is retained. Viability of the cells can be measured in CFU/ml by plating a dilution of the attenuated cells on suitable YEG agar plates. Typically, in the method of the invention for producing a cheese, a cheese analogue or a cheese-derived product, the cheese, cheese analogue or cheese-derived product is contacted with a population of cells, which cell population comprises attenuated cells. Typically the population of cells comprises at least 80%, preferably 90% and more preferably at least 99% attenuated cells.

By the term proteases we mean enzymes that hydrolyse a protein substrate in an endo fashion and that are classified by the Nomenclature Committee of the International Union of Biochemistry and Molecular biology as EC.3.4.21 (serine endopeptidases), EC.3.4.22 (cysteine endopeptidases), EC.3.4.23 (aspartic endopeptidases), EC.3.4.24 (metalloendopeptidases) or EC.3.4.99 (endopeptidases of unknown catalytic mechanism).

By the term peptidases we mean enzymes that hydrolyse a protein or peptide substrate in an exo-fashion, i.e. from either the N-terminal (e.g. aminopeptidases) or the C-terminal (e.g. carboxypeptidases) side of the substrate and that are classified by the by the Nomenclature Committee of the International Union of Biochemistry and Molecular biology as EC.3.4.11 (aminopeptidases), EC.3.4.13 (dipeptidases), EC.3.4.14 (dipeptidyl- and tripeptidyl-peptidases), EC.3.4.15 (peptidylpeptidases), EC.3.4.16 (serine-type carboxypeptidases), EC.3.4.17 (metallocarboxypeptidases), EC.3.4.18 (cysteine-type carboxypeptidases) or EC.3.4.19 (omega peptidases).

By the term lipase or esterase we mean enzymes that belong to the enzyme class E.C.3.1.1.

By the term decarboxylases we mean enzymes that belong to the enzyme class EC.4.1.1 and that convert amino acids into their corresponding amines and $CO_2$ or that convert alpha-ketoacids into their corresponding aldehydes and $CO_2$.

By the term amine oxidases we mean enzymes that belong to the class EC.1.4.3 and that convert primary amines into their corresponding aldehydes and ammonia by oxidative deamination.

By the term aldehyde dehydrogenase we mean enzymes that belong to the enzyme class EC.1.2 and that convert aldehydes into their corresponding acids in the presence of an electron- and/or hydrogen acceptor such as $NAD^+$ or $NADP^+$ (EC1.2.1), a cytochrome (EC1.2.2), oxygen (EC1.2.3) and a disulphide (EC1.2.4).

By the term alcohol dehydrogenase we mean enzymes that belong to the enzyme class EC.1.1 and that convert aldehydes into their corresponding alcohol in the presence of an electron- and/or hydrogen donor such as $NADH^+$ or $NADPH^+$ (EC1.1.1) and a cytochrome (EC1.1.2).

With the terms amino acid dehydrogenase and amino acid oxidase we mean enzymes that belong to the enzyme class EC.1.4 and that convert amino acids into their corresponding alpha-ketoacids and ammonia in the presence of an electron- and/or hydrogen acceptor such as NADH+ or NADPH+ (EC.1.4.1-dehydrogenases), a cytochrome (EC1.4.2—dehydrogenases) and oxygen (EC1.4.3-oxidases).

With the term aminotransferase or transaminase, we mean enzymes that belong to the enzyme class EC.2.6.1 and that convert amino acids into their corresponding alpha-ketoacids, in the presence of another amine accepting and oxo-donating alpha-ketoacid such as alpha-glutarate or oxaloacetate.

We have now surprisingly found that *Kluyveromyces lactis* enzymes, in the form of a cell free extract or preferably as part of attenuated *K. lactis* cells, are very efficient at degrading milk proteins into peptides and single amino acids as well as at the subsequent conversion of single amino acids to flavour molecules such as amines, ketoacids, aldehydes, ketones, alcohols, esters, acid or sulphur compounds.

By yeast enzymes we mean indigenous enzymes, so enzymes that naturally are present in the yeast cells and fulfil a natural function, e.g. metabolic function in the yeast cell.

Furthermore, we have found that attenuated *Kluyveromyces lactis* cells and/or *Kluyveromyces lactis* derived enzymes can be advantageously used to substantially enhance the rate of taste-, flavour- and texture formation of cheese, cheese analogues or cheese-derived products and/or to extend the range of tastes, flavours and textures of cheese, cheese analogues or cheese-derived products. We have found that in the cheese producing process, advantageously attenuated *K. lactis* cells and/or intracellular enzymes derived from *K. lactis* can be used. Preferably, cell-free extracts of *K. lactis* are used as source for *K. lactis* derived enzymes. The main activity of the intracellular enzymes derived from *K. lactis* comprises preferably proteases, lipases, esterases and/or other ripening enzymes as mentioned above. Preferably other purified enzyme activities, for example β-galactosidase, should not form the main activity of *K. lactis* derived enzymes to be used in the cheese making process of the invention. For example, the use of Maxilact (DSM Delft, Holland), which is a commercial lactase preparation, is preferably not comprised in the cheese making process of the present invention. β-galactosidase does not have a function in the ripening of the cheese and therefore is less desired.

In one aspect the invention provides a process for producing a cheese, a cheese analogues or a cheese-derived products, which method comprises contacting a cheese, a cheese analogue and/or a cheese-derived product or a precursor thereof with a *Kluyveromyces lactis* cell or an enzyme derived therefrom. Preferably, the contacting step of the method of the invention is carried out under conditions suitable for ripening to occur The *Kluyveromyces lactis* cell suitable for use in a process of the invention is preferably an attenuated *Kluyveromyces lactis* cell, more preferably the *K. lactis* cells are attenuated by a microwave treatment. Similarly, the enzyme used in a process of the invention can be an enzyme from an attenuated yeast cell.

The enzyme for use in a process of the invention may be a protease and/or a peptidase, preferably an endoprotease, an aminopeptidase or a carboxypeptidase. The carboxypeptidase is preferably carboxypeptidase Y.

Further, suitable enzymes for use in a process of the invention include those belonging to the class of lipases and esterases.

In addition, suitable enzymes include those belonging to classes of enzymes that convert amino acids into flavour compounds, preferably carboxylases, amine oxidases, aldehyde reductases, aldehyde oxidases, amino acid oxidases, amino acid dehydrogenases and aminotransferases or transaminases.

The yeast cell for use in a method of the invention may be a modified yeast so that it preferably over-expresses a protease, a peptidase, a lipase, a esterase or an enzyme that converts an amino acid into a flavour compound of the invention. A modified cell for use in a process of the invention may be a genetically modified cell, for example a recombinant cell or a cell identified through a random mutagenesis screening. Enzymes derived from a modified cell may also be used in the process of the invention.

EXAMPLE 1

Culturing of *Kluyveromyces lactis*

Figure 1:
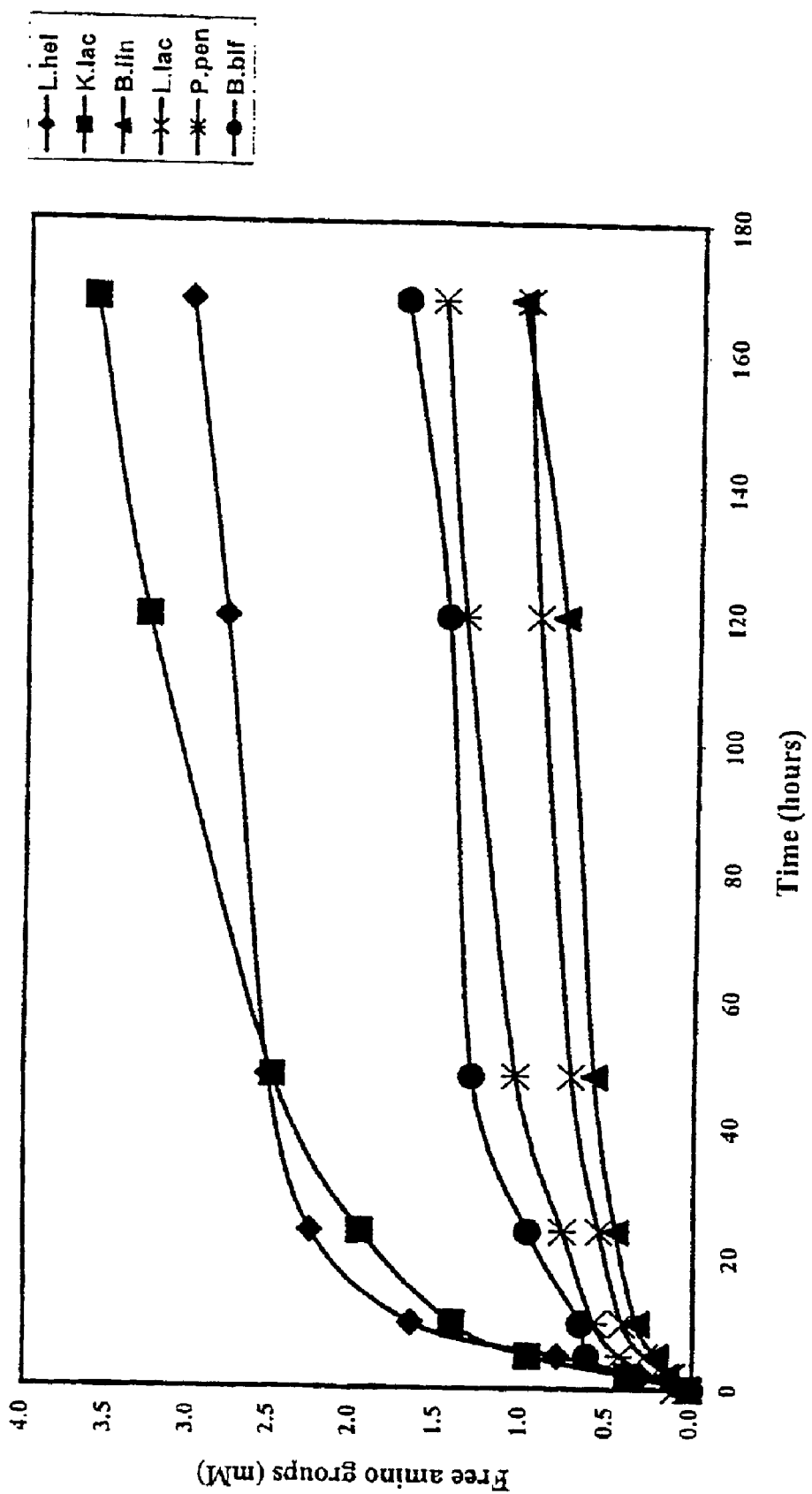
FIG. 1 shows the release of free amino groups during a kinetic degradation of beta-casein. For details see Example 4.

*Kluyveromyces lactis* was grown in a liquid YEG-medium (10 g/l Yeast extract, 20 g/l Bactopeptone and 20 µl dextrose), pH=6.5 at 30° C. Culturing proceeded in 3 steps.

Step 1—Preparation of Frozen Inoculation Material

In the first step, very dense cell suspensions were prepared in order to be used as inoculation material in subsequent fermentations. Three 500 ml bottles each containing 330 ml of YEG medium were inoculated with one yeast colony coming from a YPD (Yeast Peptone Dextrose) plate. The bottles were incubated in a rotary shaker at 220 rpm for 48 hrs at 30° C. Glycerol was then added to a final concentration of 15% after which the cell suspension was stored at −80° C.

Step 2—Pre-Culture

Three subcultures at 2% were carried out at 12 hours intervals. The first two subcultures were carried out in tubes of 10 ml of YEG medium and the last one was carried out in a 250 ml bottle containing 50 ml of YEG medium.

Step 3—Large Scale Culture

Three bottles of 500 ml containing each 330 ml of YEG medium were used for the culture. Five milliliters of the pre-culture (step 2—i.e. 1.5%) was used for each bottle. At 12 hours, the culture was in the early exponential growth stage and the OD at 650 nm was 1.5 to 2. Cells were collected by centrifugation at 18,900 g for 20 minutes at 4° C. and washed twice with cold sterile distilled water. The cell pellets were stored at −20° C.

EXAMPLE 2

Preparation of a Cell Free Extract of *Kluyveromyces lactis*

Frozen cell pellets, prepared according to Example 1 were thawed on an ice bed and resuspended in 50 ml of cold sterile distilled water (OD at 650 nm=30–40) and subsequently disrupted at 1000 Bars in a refrigerated French pressure cell. Undisrupted cells and cells debris were removed by centrifugation at 39,200 g for 20 minutes at 4° C. and the collected supernatant was sterilised by filtration (0,45 micron then 0,20 micron), distributed in sterile Eppendorfs vials and stored at −20° C. until use.

The protein content of the cell free extracts was determined according to the Lowry method using bovine serum albumin as a standard (Lowry et al 1951). Typically, the cell free extract had a protein content of 2-4 mg/ml depending on the strain.

EXAMPLE 3

Preparation of Beta-Casein

In order to determine the peptidase activity of the cell free extract of *K. lactis* and/or lactic acid bacteria, beta-casein was chosen as a substrate because it is a representative cheese substrate and also the most hydrolysed casein fraction in ripened semi-hard cheeses (Ferranti et al., 1997 and Gouldsworthy et al., 1996).

Beta-casein was purified from milk as described in Le Magnen and Maugas (1992). It was subsequently partially hydrolysed using the endoproteases trypsin (EC.3.4.21.4) and chymotrypsin (EC.3.4.21.1) in order to generate small peptides that are more suitable substrates for the peptidases in the cell free extracts described in Example 2 above. Trypsin was chosen because it has the same specificity as the endogenous milk enzyme plasmin (EC.3.4.21.7).

A solution of beta-casein, at 10 mg/ml in sterile distilled water, was hydrolysed by a mixture of trypsin (5000 K, Novo Industry A/S, Copenhagen, Denmark) and chymotrypsin (Sigma), both at an enzyme/substrate ratio of 1/1 000 (w/w), for 3 h at 37° C. and at pH 7.2 which was kept constant by adding 0.5 M NaOH. After the time indicated, the enzymes were inactivated by heating the solution for 20 minutes at 80° C. The solution was lyophilised and stored at 4° C. until use, (Lemée et al., 1998), Lait, 78, 227–240). The final degree of hydrolysis was 16% as deduced from the determination of free amino-groups using the modified colorimetric ninhydrin method for peptidase assay as described by Doi et al (1981). The peptide mixture was characterised by mass spectrometry and contained 34 different peptides with molecular weights ranging from 373–3864.

EXAMPLE 4

Proteolytic Degradation of Beta-Casein by a Cell-Free Extract of *Kluyveromyces lactis* and some Lactic Acid Bacteria One milliliter of a solution containing 24.8 $\mu$M prepared according to example 3, was incubated with 125 $\mu$g of cytoplasmic protein of *Kluyveromyces lactis* or lactic acid bacteria and incubated at 24° C. in a buffer of 50 mM sodium phosphate at pH 5.7. Duplicate samples were taken at zero time and at 2, 5, 10, 24, 48, 120 and 168 hours. The enzyme reaction was stopped by heating the samples in a 100° C. water bath for 20 minutes. Subsequently, samples were precipitated with a 10-fold volume of ethanol.

The proteolytic activity of the cell free extract was determined by analysing the increase in free amino groups according to the method of Doi et al (1981), using methionine as a standard. The degree of proteolysis corresponded to the difference between the free amino groups at a certain time and at zero time and was expressed in mmole equivalents methionine. Free proline was not quantified with this method because it lacks a free amino group. Heat-treated cell free extracts were used as a control.

Free amino acids were identified and quantified as follows: at indicated time points, the boiled samples were taken and precipitated with sulphosalicylic acid according to the method of Mondino et al., (1972). The supernatant was analysed by ion exchange chromatography where the free amino acids were detected by post-column derivatization using ninhydrin, essentially as described by Mondino et al (1972).

FIG. 1 shows the increase in free amino groups as a function of time for the cell free extract of *K. lactis* and several lactic acid bacteria. The figure clearly shows that *K. lactis* is far more active than the lactic acid bacteria.

Table 1 summarises the liberation of individual amino acids after 168 hours expressed as percentage of the total amount of each amino acid present in beta-casein. The added amount of cell free extract protein was the same in all incubations.

*K. lactis* is the most active of all strains tested in liberating tyrosine (112%), phenylalanine (94%), methionine (89%), leucine (91), isoleucine (79%), valine (90%) and the total amount of free amino acids (88%). Only in the case of proline was *Lactobacillus helveticus* more efficient (74%) than *K. lactis* (55%), which was still more active than the other 4 strains.

TABLE 1

Free amino acids after 168 hours of hydrolysis of beta-casein by cell free extracts of the indicated micro-organisms. Expressed as percentage of the total amount of each amino acid present in beta-casein. The values that are underlined and bold are the highest for a given amino acid.

| Amino acid | Kluyveromyces lactis CBS 2359 | Lactobacillus helveticus CNRZ-32 | Pediococcus pentosaceus 559 | Bifidobacterium bifidum CIP567 | Leuconostos lactis CNRZ1091 | Brevibacterium linens 550 |
|---|---|---|---|---|---|---|
| Proline | 55 | 74 | 0 | 38 | 3 | 17 |
| Tyrosine | 100 | 83 | 33 | 52 | 33 | 57 |
| Phenylalanine | 94 | 79 | 31 | 46 | 17 | 64 |
| Methionine | 89 | 72 | 52 | 54 | 42 | 28 |
| Leucine | 91 | 80 | 45 | 41 | 34 | 38 |
| Isoleucine | 79 | 72 | 50 | 38 | 31 | 18 |
| Valine | 90 | 79 | 46 | 41 | 24 | 18 |
| Total amino acids | 88 | 75 | 36 | 43 | 28 | 22 |

EXAMPLE 5

Formation of Flavour Compounds by Cell Free Extracts of *Kluyveromyces lactis* and Several Lactic Acid Bacteria The formation of flavour compounds from amino acids was measured by incubating a mixture of amino acids with cell free extracts of the microorganisms indicated. Amino acids were selected on the basis that their degradation is known to result in typical cheese flavours. The composition of the incubation mixture was as shown in Table 2.

TABLE 2

Formation of cheese flavour components; composition of the incubation mixtures.

| Compound | Concentrations |
|---|---|
| L-Methionine | 3.7 mM |
| L-Isoleucine | 7.9 mM |
| L-Leucine | 13.6 mM |
| L-Valine | 13.4 mM |
| L-Phenylalanine | 5.2 mM |
| L-Tyrosine | 2.9 mM |
| α-ketoglutaric acid | 95.4 mM |
| Piridoxal phosphate | 50 μM |
| Thiamine pyrophosphate | 50 μM |
| Cell free extract | 125 μg protein/ml |
| Sodium phosphate buffer | 50 mM |
| PH | 5.7 |

α-ketoglutaric acid was added for transaminase reactions. The cofactors piridoxal phosphate and thiamine pyrophosphate were added as cofactors for transamination reactions and decarboxylation reactions.

The mixtures were incubated at 24° C. and 5 ml samples were taken at 0, 24 and 168 hours and subsequently analysed by HPLC and Head Space GC-MS; see Table 3 for an overview of the analytical method used.

The samples were also subjected to a sniffing test that consisted of a semi-quantitative judgement and qualitative description of the flavours of the mixtures. This was carried out by a panel of 14 people using 4 ml of each incubation mixture per person.

TABLE 3

Analytical methods used for the separation and the detection of the possible compounds present in the samples.

| Compounds | Separation | Detection | Detection Threshold (μg/g) |
|---|---|---|---|
| α-ketoacids | HPLC | UV | 3 |
| α-hydroxyacids | HPLC | UV | 30 |
| Other acids | HPLC | UV | 30 |
| Alcohols | CG | MS | 0.002 |
| Aldehydes | CG | MS | 0.001 |

HPLC-Analysis

HPLC was used for the quantitative analysis of non-volatile ketoacids, hydroxyacids and other acids that were derived from the amino acids (in brackets) by transamination: α-phenylpyruvic acid (Phe), para-hydroxyphenyl-pyruvic acid (Tyr), α-ketoisocaproic acid (leu), α-keto-β-methylvaleric acid (Ile) and α-ketoisovaleric add (Val). The consumption of α-ketoglutaric acid due to these transamination reactions was also measured by HPLC.

Just before analysis, the samples were thawed, homogenised and diluted 10-fold with the HPLC-eluant (0.01 N $H_2SO_4$) and centrifuged. Injections were done using an automatically controlled fraction collector. The loop volume was about 20 μl and the assays were done in full loop. The volume for the injection was 40 μl. The flush volume was 30 μl. The separation and detection conditions were as follows: the samples were injected on a reversed phase Aminex AS column (300×7.5 mm, Biorad, Richmond, USA) which was operated under isocratic conditions at a flow rate of 1 ml/min (Beckman pump) and an oven temperature of 55° C. The UV detection was carried out at 210 nm using a Beckman detector. All data were analysed with the Gold data management system version 8.1 also provided by Beckman.

The column was calibrated for each of the compounds listed in Table 4. Hereto, several concentrations of the compounds were applied to the HPLC and their "response coefficient", equalling the slope of the linear regression line obtained after plotting the concentration of the standard compound versus the surface of the peak, was determined.

TABLE 4

Non volatile compounds analysed by HPLC

| Compound | Originating from |
|---|---|
| α-ketoglutaric acid | — |
| α-ketoisovaleric acid | Valine |
| α-keto-β-methylvaleric acid | Isoleucine |
| α-ketoisocaproic acid | Leucine |
| α-phenylpyruvic acid | Phenylalanine |
| Para-hydroxyphenylpyruvic acid | Tyrosine |
| Isobutyric acid | Valine |
| α-hydroxyisovaleric acid | Valine |
| α-hydroxyisocaproic acid | Leucine |
| α-hydroxy-β-methylvaleric acid | Isoleucine |
| Isovaleric acid | Leucine |

Methionine-derived flavour compounds could not be determined by this HPLC method.

GC-MS

With GC-MS the following volatile compounds were detected: benzaldehyde (from Phe via transamination, decarboxylation, reduction and other reactions)

2-methylbutanal (from Ile via transamination, decarboxylation), 3-methylbutanal (from Leu via transamination and decarboxylation), 2-methylpropanal (from Val via transamination/deamination and decarboxylation), 2-methylpropanol (from Val via transamination/deamination, decarboxylation and reduction), 2-methylbutanol (from Ile via transamination/deamination, decarboxylation and reduction).

The headspace volatile compounds of the samples were isolated and analysed by a dynamic headspace analyzer Tekmar 3000 (Tekmar Inc., Cincinnati, Ohio, USA) coupled to a HP5890A gas chromatograph (Hewlett Packard, Avondale, Pa., USA).

The samples were thawed just before analysis, homogenised and diluted ten-fold in boiled milli-Q water. 3 g of the dilution was weighted in a 35 ml non-fritted sparger. All samples were purged with 35 ml/min ultra pure helium gas at 65° C. for 15 min to isolate headspace volatiles which were adsorbed on a Vocarb 3000 trap (stainless steel tube packed with 10 cm carbopack B, 6 cm carboxen 1000, 1 cm Carboxen 1001, Supelco, Bella Fonta, Pa. USA). The trapped compounds were thermally desorbed at 250° C. during 4 min and cryofocused at −100° C. before being injected by heating at 270° C. They were separated on a HP5 capillary column (60 m×0.32 mm×1.0 μm film thickness) under the following conditions:

carrier gas: helium, 29 cm/s at 35° C.;

temperature program: 35° C. for 5 min heating rate: 5° C./min to 140° C. then 15° C./min to 250° C.

The other operating conditions were: "moisture control module": 200° C.; valve and transfer lines: 200° C.; trap cleaning by baking at 260° C. for 8 min to remove residual compounds. The GC column was connected without splitting to the ion source of a HP7972A quadruple mass spectrometer (interface line 280° C.), operating in the scan mode within a mass range of m/z 25–300 at 2.5 scan/s. Ionisation was carried out by electronic impact at 70 eV; calibration was carried out by autoturing. Quantification was performed by integrating the peak areas of total ion chromatograms (TIC) using the Hewlett Packard Chemstation software. Compounds were tentatively identified by computer matching of mass spectral data with those in Hewlett Packard Chemstation NIST 75K Mass Spectral Database and by comparing their mass spectra and retention times to those of standard compounds.

TABLE 5

Formation of flavour compounds after 168 hours from a mixture of amino acids by cell free extracts of Kluyveromyces lactis (K. lac), Lactobacillus helveticus (L. hel) and Brevibacterium linens (B. lin) or a mixture (mix) of L. hel and K. lac (each 125 μg/ml) versus a blanc incubation (=mixture of amino acids with water instead of cell free extracts).

| Compound | K. lac 106 | K. lac 2166 | L. hel 735 | L. hel CNRZ-32 | B. lin 550 | B. lin 100 | Mix | Blanc |
|---|---|---|---|---|---|---|---|---|
| α-ketoglutaric acid (consumption in mM) | 11.7 | 14.3 | 21.5 | 15.8 | 8.9 | 14.4 | 15.1 | −1.4 |
| Non-volatiles | | | | | | | | |
| β-phenylpyruvic acid (mM) | 0.3 | 0.1 | 7.4 | 6.7 | 3.1 | 0.2 | 7.3 | 0.0 |
| Para-hydroxyphenylpyruvic acid (mM) | 0.1 | 0.04 | 2.0 | 1.7 | 0.9 | 0.1 | 1.9 | 0.0 |
| α-ketoisocaproic acid (mM) | 1.1 | 0.5 | 6.2 | 5.2 | 0.9 | 0.3 | 6.1 | 0.0 |
| α-keto-β-methylvaleric acid (mM) | 1.1 | 0.5 | 1.8 | 1.8 | 1.1 | 0.2 | 2.2 | 0.0 |
| α-ketoisovaleric acid (mM) | 0.2 | 0.0 | 0.7 | 0.9 | 0.2 | 0.0 | 0.6 | 0.0 |
| volatiles | | | | | | | | |
| 2-methylpropanal (μM) | _11.5_ | 1.6 | 0.0 | 0.1 | 0.1 | 0.0 | 4.1 | 0.0 |
| 2-methylpropanol-1 (μM) | 0.1 | 0.0 | _0.3_ | _0.3_ | ?? | ?? | 0.3 | 0.1 |
| 3-methylbutanal (μM) | _38.5_ | _14.8_ | 0.0 | 0.1 | 0.1 | 0.1 | 91.2 | 0.0 |
| 2-methylbutanal (μM) | _27.9_ | _6.7_ | 0.0 | 0.1 | 0.0 | 0.0 | 18.1 | 0.0 |
| 2-methylbutanol-1 (μM) | 0.01 | 0.0 | 0.0 | 0.0 | 0.0 | 0.0 | 0.0 | 0.0 |
| Dimethylsulfide (μM) | 0.1 | 0.2 | 0.2 | 0.3 | _0.7_ | _1.2_ | 0.4 | 0.0 |
| Benzaldehyde (μM) | 0.9 | 0.8 | _30.9_ | _44.1_ | 2.6 | 1.4 | 32 | 0.0 |
| Total production | | | | | | | | |

TABLE 6

Sniffing test results of the incubations of amino acids with cell free extracts (Table 5). Of each incubation mixture two tubes were present in the series: one to be analysed after 24 hours, the second one after 168 hours. The analysis was performed blind and the tubes were placed in random order. The quantitative data represent the number of people giving the indicated score (low, medium or high smell level or none).

| Strain | Smell level after 24/168 hours | | | | Number of people: Description |
|---|---|---|---|---|---|
| | none | low | Medium | high | |
| Water | 14/14 | 0/0 | 0/0 | 0/0 | — |
| K. lac 106 | 0/0 | 0/0 | 8/4 | 6/10 | 6: Cheese aperitif cracker - 4: roasted/toasted - 3: pleasant, smoked - 2: Malted; unpleasant; aldehyde; yeast; honey (cooked sugar); socks |
| K. lac 2166 | 0/1 | 3/4 | 8/7 | 3/2 | 7: Cheese aperitif cracker - 4: malted - 3: toasted cheese (Camembert) - 2: smoked; honey (cooked sugar) - 1: pleasant; unpleasant; socks; bacterial culture |
| L. hel CNRZ-32 | 5/1 | 9/7 | 0/4 | 0/2 | 4: benzaldehyde (bitter) - 2: very light cheese acid/yogurt honey (cooked sugar); yeast - 1: rotten, fetid, bacterial culture |
| B. lin 550 | 3/0 | 10/8 | 1/6 | 0/0 | 9: cheese (intense, goat, Camembert) - 3 unpleasant (feet) - 2: yoghurt, fermentation smell, rancid - 1: rotten |
| B. lin 100 | 2/0 | 3/0 | 8/7 | 1/7 | 10: (old) cheese (Camembert; Roquefort) - 5: unpleasant feet - 4: rotten (cauliflower) - 2:; rank acid - 1: cheese aperitif cracker; bread; pleasant; yoghurt; fermentation; humidity; stinking cheese; sulphur; moldy; sewers. |
| Blanc | 10/1 | 4/9 | 0/4 | 0 | 3: unpleasant; cheese - 2: yeast extract - 1: cauliflower; yogurt; cooked sugar; bacterial culture; rotten |

The formation of α-ketoacids from amino acids is summarised in Table 5. Only in the case of the two Lactobacilli strains and *B. linens* strain 550 was there a quantitative correlation between the formation of α-ketoacids and the consumption of α-ketoglutaric acid. In case of the two *K. lactis* strains and *B. linens* AS100 products other than those determined by the HPLC-analysis were apparently being formed.

With respect to the formation of the volatile compounds, remarkable differences were observed between *K. lactis, L. helveticus* and *B. linens*. No major qualitative differences were found for the two different strains per type of microorganism. Table 3 shows that both strains of *K. lactis* very efficiently produced 2-methylbutanal, 3-methylbutanal, 2-methylpropanal and some benzaldehyde. *L. helveticus* produced mainly benzaldehyde and a little 2-methylpropanal, while *B. linens* produced some benzaldehyde and sulphur compounds. In the case of the mixture of cell free extracts, all volatiles were formed.

The results of the sensory analysis are summarized in Table 6 and show that *K. lactis* was capable of producing medium/high smell levels compared to *L. helveticus* (low) and *B. linens* (low/medium). The panel positively judged the flavour developed by *K. lactis* and characterised it predominantly as cheese-like flavour.

All the results obtained clearly demonstrate that *K. lactis* is capable of forming α-ketoacids and flavour molecules from amino acids and therefore that it can be used successfully in the ripening step of cheese, cheese analogues and cheese-derived products.

EXAMPLE 6

A Pilot Scale Cheese Making

At pilot scale pressed cheese-making was performed in order to validate our previous results in vitro with cell free extracts.

Step 1—Milk Preparation 2 vats of 26 kg of milk at 28 g/kg of fat matter were prepared with low heat skimmed milk powder and commercial raw cream.

Firstly skimmed milk was prepared with Low heat powder 10 g powder in 100 g water. The fat content of a commercial raw cream was measured with the Dairy Lab, and a certain quantity of cream was added to the skimmed milk to result in 28 g/kg of fat matter in the milk.

In our case, we did:

| | Each vat of 26 reconstituted milk |
|---|---|
| Low heat powder | 2.17 kg |
| Osmosed water | 21.68 kg |
| Raw commercial cream (at 333.7 g/kg of fat matter) | 2.15 kg |

Step 2—Preparation of Attenuated *K. lactis*

13 Bottles of 500 mL containing each 400 mL of YEG medium were used for the culture. The cell pellets were resuspended after the final centrifugation in 260 mL of SDW and distributed in 10*10 mL insterile tubes. All tubes were placed in a water bath at 20° C. Microwave treatment was carried out on each, which were finally put together in a sterile bottle and kept cooled before use.

Step 3—Cheese Preparation

The 2 vats containing each 26 kg of reconstituted milk are warmed at 34° C. with a warm water circulation bath. The pH of the is 6.65 in the two vats.

5.2 ml of a 500 mg/L $CaCl_2$ solution are added to each vat

A commercial lactococci starter is added at 4 U/100 L, which represents in our case 1.04U for 26 kg of milk. The mixture is stirred and left without stirring until the pH has reached 6.55 after about 80 minutes of incubation. At the same moment, in the trial vat, the attenuated starter is added at 1% (w/w), which represents 260 ml of a microwave treated concentrate.

9.75 ml of a 3-fold diluted chymosin product (Maxiren-600 from DSM) are added in each vat. Incubation proceeds for 30 minutes in a 28° C. room until a firm coagulum is formed.

The formed curd is cut twice with the special equipment and the cut particles are "healed" for 10 minutes and then stirred slowly (speed 2 out of 5 total speeds) for 10 minutes. 20% of the whey (5.2 kg) in each vat is taken off and is replaced by the same quantity of 35° C. demineralized water. The mixture is stirred again for 15 minutes at the same low speed.

After the second stirring operation, the wey fraction was taken off and curd content of each vat is divided in six round moulds. The room temperature is fixed at 26° C.

After 10 minutes, a pressure of 6 $g/cm^2$ is put on each mould. After 15 minutes, the moulds containing the cheeses are turned over and the same pressure is applied for 15 minutes again. During 3 hours, each 15 minutes the same operation is performed and the cheese reaches pH 5.2. The room temperature is fixed at 16° C. and the mould cheeses are conditioned for the night under the same pressure.

After 14 hours, the cheeses are brined in a 15% NaCl solution for 50 minutes, then drained for 5 hours, bisected and vacuum packed to be ripened at 12° C.

EXAMPLE 7

Attenuation of *Kluyveromyces lactis*

Cells of *Kluyveromyces lactis* were cultured as described in example 1 and harvested in the early exponential phase under sterile conditions by centrifugation at 18,900 g for 20 minutes at 4° C. The cells were washed twice with sterile distilled water (SDW). The cell pellets were resuspended in 100 ml of SDW after the final centrifugation and distributed in 10*10 ml in sterile tubes. All tubes were placed in a water bath at 20° C.

Microwave treatment was carried out using a Philips AVM 025 microwave oven (absorbed power: 1200 W/230 V) equipped with a timer and variable power setting. Each 10 ml sterile tube got a microwave treatment of 650 W for 13 seconds. The microwave treatment had no significant effect on the peptidase activity, whereas 99% of the cells were killed.

EXAMPLE 8

Validation of our Attenuated Starter in a Pilot Scale Cheese Making and Measurement of Proteolysis and Flavour Compounds Formation A pilot scale cheese experiment was performed as described in example 6. Attenuation of *Kluyveromyces lactis* was realized as described in example 7. 13 bottles of 500 ml containing each 400 ml of YEG medium (5.2 liters of culture in total) were used for the culture. The cell pellets after the final centrifugation were resuspended in 260 ml of SDW and distributed in 10*10 ml in sterile tubes. All tubes were placed in a water bath at 20° C. Microwave treatment was carried out on each tube, which were at the end put together in a sterile bottle kept in cold before used.

The cheese characteristics at day +1 are described in Table 8. The different measurements were performed twice on half cheeses for the blank and for the trial cheese containing 1% of attenuated *K. lactis*.

TABLE 8

Cheese biochemical characteristics at day + 1.

| Day + 1, trial 1 | Blank | Cheese + K.I |
|---|---|---|
| Weight (g) | 261 +/− 18 | 271 +/− 11 |
| PH | 4.94 | 4.94 |
| Dry Matter (%) | 41.25 | 40.55 |
| Fat (%) | 19.7 | 19.7 |
| FDM (%) | 47.8 | 48.6 |
| MFFS (%) | 73.2 | 74 |
| Salt (%) | 0.85 | 0.95 |
| S/M (%) | 1.4 | 1.6 |
| Residual lactose (g/l) | 0.8 | 0.9 |

Figure 2:
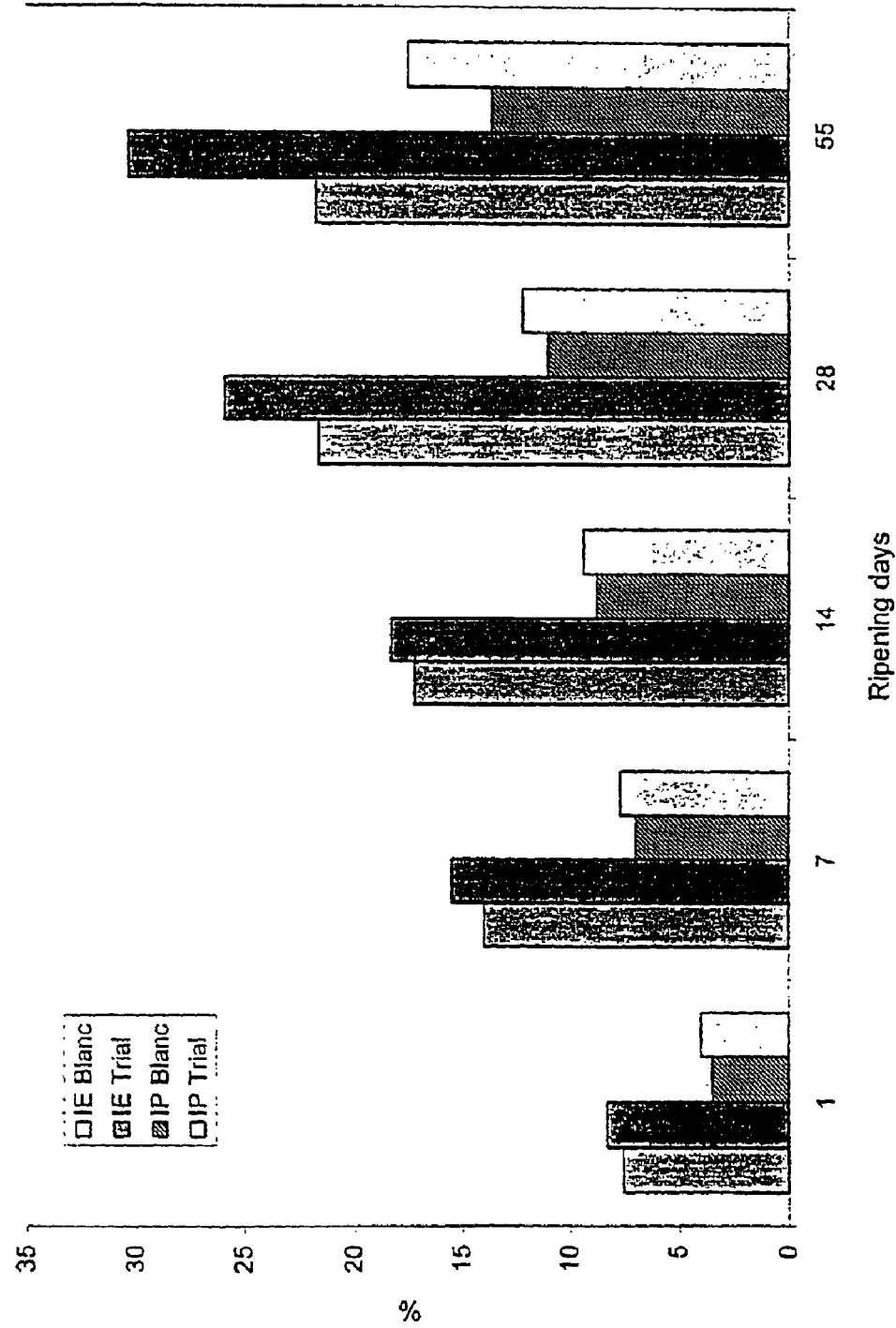
FIG. 2 shows the enhancement of the proteolysis in the cheeses containing the attenuated yeast.

FDM: FAT IN THE DRY MATTER
MFFS: MOISTURE IN THE FAT-FREE SUBSTANCE
S/M: Salt-in-moisture Cheese samples were analyzed at day +1. +7, +14, +28 and +55 for total nitrogen (TN), Non Protein Nitrogen (12% trichloroacetic acid (TCA)-soluble N) and Non Casein Nitrogen (Soluble Nitrogen at pH 4.6) by the Kjeldahl method (IDF, 1993). The evolution of the ripening indices in both control and trial cheeses is presented in the FIG. 2, which clearly shows the enhancement of the proteolysis in the cheeses containing the attenuated yeasts.

The ripening indices were defined as:
IE=NCN/TN
IP=NPN/TN

The neutral volatile compounds were determined by CG-MS on cheese aqueous extracts in the same conditions as described in the example 5. The results are presented in the Table 9.

TABLE 9

Neutral volatile compounds present at day + 1 and day + 45 in both control and trial cheeses (arbitrary area units).

|  | Blank day + 1 | Trial day + 1 | Blank day + 45 | Trial day + 45 |
|---|---|---|---|---|
| Aldehydes |  |  |  |  |
| Acetaldehyde | — | 38 | — | 262 |
| 3-Methylbutanal | 3 | 10 | 4 | 22 |
| Pentanal Benzaldehyde | 3 | 2 | 1 | 4 |
|  | 3 | 1 | 5 | 2 |
| Nonanal | 1 | — | 1 | 1 |
| Alcohols |  |  |  |  |
| 2-Methylpropanol-1 | — | 53 | 26 | 132 |
| 3-Methylbutanol-1 + 2-Methylbutanol-1 | — | 602 | 133 | 655 |
| 1-Hexanol | 2 | — | 2 | 3 |
| Esters |  |  |  |  |
| Ethyl acetate | 2 | 773 | 373 | 774 |
| Ethyl propanoate | — | 1 | 1 | 5 |
| n-propyl acetate | — | — | 1 | 6 |
| Ethyl butanoate | — | 20 | 8 | 64 |
| Ethyl hexanoate | — | 3 | 2 | 23 |
| Ethyl octanoate | — | — | — | 6 |

The two alcohols 3-Methylbutanol-1 and 2-Methylbutanol-1 were coelutated, so in the table the two area concerning both compounds were summed. Table 9 clearly shows an increase of aroma compounds like aldehydes, alcohols and esters in the trial cheese containing the attenuated yeast. For some compounds the increase was already noted at day 1. It is clear that there is a positive effect on the volatile aroma compounds formation in the cheese due to the attenuated yeast.

REFERENCES

Conner, T. (1988) Advances in accelerated ripening of cheese. Cult Dairy Prod. J. 23, 21–25

Doi, E., Shibata, D., and Matoba, T. (1981) Modified colorimetric ninhydrin methods for peptidase assay. Anal. Biochem. 118, 173–184.

El Soda, M. and Pandian, S. (1991) Recent developments in accelerated cheese ripening. Journal of Dairy Science 74, 2317–2335.

El Soda, M., Chen, B., Riesterer, B. and Olson, N. (1991) Acceleration of low-fat cheese ripening using lyophilised extracts or freeze shocked cells of some cheese related micro-organisms. Milchwissenschaft 46, 358–360.

Ferranti et al., (1997) Lait, 77, 683–697

Foster, E. M., Nelson, F. E., Speck, M. L., Doetsch, R. N. and Olson, J. C. (1983) "Dairy Microbiology" Ridgeview Publishing, Atascadero, Calif.

Fox et al. (1996) Anthonie van Leeuwenhoek, 70:271–297

Fox, P. F. (1989) Proteolysis during cheese manufacture and ripening. J. Dairy Res. 72, 1379–1400

Gao, S., Broadbent, J. R., Johnson, M. E., Weimer, B. C., and Steele, J. L. (1997) Aromatic amino acid catabolism by lactococci. Lait 77, 371–381.

Gobbetfi, M., Fox, P. F. and Stepaniak, L. (1996) Esterolytic and lipolytic activities of mesophilic and thermophilic lactobacilli. Italian Journal of Food Science 2, 127–137.

Gouldsworthy et al. (1996) Int. Dairy J. 6, 781–790

Klein, N. and Lortal, S. (1999) attenuated starters: A powerful means to influence cheese ripening—a review. Int. Dairy J. submitted for publication.

Law, J. and Haandrikman, A. (1997) Proteolytic enzymes of lactic acid bacteria. International Dairy Journal 7, 1–11.

Lemée, R., Gagnaire, V., and Maubois, J. L. (1998) Strain variability of the cell-free proteolytic activity of dairy propionibacteria towards β-casein peptides. Lait 78, 227–240.

Lowry, O. H., Rosebrough, N. J., Farr, A. L, and Randall, R. J. (1951) Protein measurement with the folin phenol reagent. J. Biol. Chem. 193, 265–275.

Le Magnen, C., Maugas, J. J., (1991) Method and device for obtaining beta casein. International Patent Application WO92/000017 to EURIAL Mondino, A, Bongiovanni, G., Fumero, S., and Rossi, L. (1972) An improved method of plasma deproteinisation with sulphosalicylic acid for determining amino acids and related compounds. J. of Chromatography 74, 255–263.

Petterson, H. and Sjöström, G. (1975) Accelerated cheese ripening. A method of increasing the number of lactic starter without detrimental effect of the cheese making process and its effect on cheese ripening. Journal of Dairy Research 42, 313–326:

Tye, T. M., Haard, N. F. and Patel, T. R. (1988) Effects of bacterial protease on the quality of Cheddar cheese. Can. Inst. Food Sci. Technol. J. 21, 373–377

Shakeel-Ur-Rehman, McSweeney, P. L. H., and Fox, P. F. (1998) Protocol for the manufacture of miniature cheeses. Lait 78, 607–620.

Singleton, P. (1994) Dictionary of Microbiology & Molecular Biology, page 784, J. Riley & Son, New York Urbach, G. (1995) Contribution of lactic acid bacteria to flavour compound formation in dairy products. International Dairy Journal 5, 877–903.

Yvon, M., Berthelot, S., and Gripon, J. C. (1998) Adding α-keto-glutarate to semi hard cheese curd highly enhances the conversion of amino acids to aroma compounds. Int. Dairy J. 8, 889–898.

Yvon, M., and Gripon, J. C., (1997) Use of keto acids to enhance the flavour of cheese products International Patent Application WO 9848645 to INRA

What is claimed is:

1. A process for ripening a cheese, a cheese analogue, or a cheese-derived product, which process comprises adding to said cheese, cheese analogue or cheese-derived product, or to milk, butter or cheese curds or mixtures thereof within a cheese-making process, an attenuated culture of *Kluyveromyces lactis*.

2. A process according to claim 1, wherein the *K. lactis* cells are modified to over-express an enzyme which enzyme is a protease, a peptidase, a lipase, an esterase, or an enzyme that converts an amino acid into a flavour compound.

3. A *Kluyveromyces lactis* culture wherein at least 80% of cells are killed, but not lysed.

4. The culture of claim 3, wherein more than 50% of intracellular enzyme activity is retained within the cells.

5. The culture of claim 3, wherein more than 90% of the cells in the culture are killed, but not lysed.

6. The culture of claim 3, wherein more than 90% of the intracellular enzyme activity of the cells in said culture is retained.

7. The culture of claim 3, which has been obtained by subjecting a *K. lactis* culture to microwave energy.

* * * * *